United States Patent [19]

Werner et al.

[11] Patent Number: 4,634,713
[45] Date of Patent: Jan. 6, 1987

[54] ANTIHYPERTENSIVE 3-(UREIDOCYCLOHEXYLENEAMINO)PROPANE-1,2-DIOL DERIVATIVES

[75] Inventors: Lincoln H. Werner, Summit, N.J.; Neville Ford, University City, Mo.

[73] Assignee: Ciba-Geigy Corporation, Ardsley, N.Y.

[21] Appl. No.: 767,232

[22] Filed: Aug. 19, 1985

Related U.S. Application Data

[63] Continuation of Ser. No. 499,602, May 31, 1983, abandoned, which is a continuation-in-part of Ser. No. 383,049, May 28, 1982, abandoned.

[51] Int. Cl.$^4$ .................. A61K 31/415; C07D 233/34
[52] U.S. Cl. .................................... 514/392; 546/210; 546/234; 260/239 BC; 546/278; 546/288; 260/243.3; 546/300; 548/135; 260/244.4; 548/146; 548/215; 260/245.5; 548/318; 548/320; 260/245.7; 548/503; 548/560; 514/218; 564/27; 564/47; 514/222; 514/228; 514/235; 514/274; 514/312; 514/326; 514/331; 514/340; 514/341; 514/365; 514/374; 514/415; 514/429; 514/586; 514/597; 544/58.1; 544/58.5; 544/58.6; 544/123; 544/134; 544/160; 544/165; 544/316; 546/141; 546/142; 546/165

[58] Field of Search ............... 548/320, 318, 135, 503, 548/560, 146, 215; 260/239 BC, 244.4, 245.7, 245.5, 243.3; 544/160, 165, 123, 134, 316, 58.1, 58.6, 58.5; 546/141, 142, 165, 278, 300, 288, 210, 234; 564/27, 47; 514/218, 222, 228, 235, 274, 312, 326, 331, 340, 341, 415, 429, 365, 374, 392, 586, 597

[56] References Cited

U.S. PATENT DOCUMENTS 3,852,291 12/1974 Augstein et al. ............... 548/320 X
4,041,075 8/1977 Smith ............................. 260/501.17
4,131,685 12/1978 Smith ............................. 514/522
4,171,374 10/1979 Smith ............................. 560/9 X
4,260,632 4/1981 Smith ............................. 424/285
4,387,099 6/1983 Smith ............................. 546/291 X
4,515,814 5/1985 Wick et al. ..................... 514/652
4,521,414 6/1985 Chiou et al. .................... 514/229

FOREIGN PATENT DOCUMENTS 0000355 1/1979 European Pat. Off. ............ 424/274
2238504 2/1973 Fed. Rep. of Germany ............ 320/

OTHER PUBLICATIONS

Chiou, G., *Biochemical Pharmacology*, vol. 30, pp. 103–106 (1981).

*Primary Examiner*—Richard A. Schwartz
*Attorney, Agent, or Firm*—Norbert Gruenfeld

[57] ABSTRACT

Certain 3-(ureidocyclohexyleneamino)propane-1,2-diol derivatives, such as the compounds of formula III below, represent novel and useful pharmaceutical agents, e.g. potent antihypertensive and cardioactive agents demonstrating both α- and β-adrenergic blocking activity.

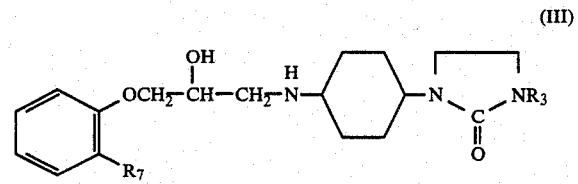

$R_3$ is hydrogen or lower alkyl;
$R_7$ is cyano, lower alkoxycarbonyl, pyrrolyl, morpholino, alkenyloxy of 3 to 6 carbon atoms, alkynyloxy of 3 to 6 carbon atoms, alkoxy of 1 to 3 carbon atoms substituted by cyclopropyl.

20 Claims, No Drawings

ANTIHYPERTENSIVE 3-(UREIDOCYCLOHEXYLENEAMINO)PROPANE-1,2-DIOL DERIVATIVES

CROSS-REFERENCE TO RELATED APPLICATION

This application is a continuation of application Ser. No. 499,602, filed May 31, 1983, now abandoned, which is a continuation-in-part of application Ser. No. 383,049, filed May 28, 1982, now abandoned.

SUMMARY OF THE INVENTION

The present invention is based on the finding that certain 3-(ureidocyclohexyleneamino)propane-1,2-diol derivatives represent novel and useful pharmaceutical agents, e.g. potent antihypertensive agents demonstrating both α- and β-adrenergic blocking activity.

The foregoing attributes render the compounds of this invention particularly useful when administered alone or in combination to mammals, including man, e.g., for the treatment or prevention of cardiovascular disorders such as hypertension and cardiac disorders, particularly coronary myocardial infarction, arrhythmia and angina. Furthermore, compounds of the invention may also be useful for the treatment or prevention of other diseases responsive to β-adrenergic blockade, e.g., nervous system disorders such as tension or anxiety, glaucoma, migraine, atherosclerosis and the like.

DETAILED DESCLOSURE OF THE INVENTION

Specifically the object of the invention relates to certain 1-aryloxy-2-hydroxy-3-(ureidocyclohexyleneamino)-propanes and derivatives useful as cardiovascular, e.g., antihypertensive and cardioactive agents, the processes for preparing same, the pharmaceutical compositions comprising said compounds, and methods of treating cardiac diseases and hypertension by administration of said compounds or pharmaceutical compositions thereof to mammals.

Particularly the invention relates to compounds of formula

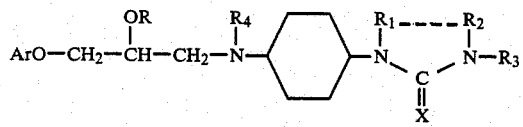

wherein
Ar represents a (monocyclic or optionally partially hydrogenated bicyclic) carbocyclic or heterocyclic optionally substituted aromatic radical;
R represents hydrogen, alkanoyl or aroyl;
$R_1$ and $R_2$ represent independently hydrogen or lower alkyl; or
$R_1$ and $R_2$ combined represent unbranched or branched alkylene of 2 to 7 carbon atoms separating the two nitrogen atoms thereto attached by 2 to 4 carbon atoms;
$R_3$ and $R_4$ independently are hydrogen or lower alkyl; and
X represents oxo (O) or thio (S); and pharmaceutically acceptable salts thereof.

Preferred are compounds of formula I as described above wherein Ar represents optionally substituted phenyl, pyridyl, naphthyl, tetrahydronaphthyl, 3,4-dihydro-1(2H)-naphthalenone, 3,4-dihydro-2(1H)-quinolone, 3,4-dihydro-1(2H)-isoquinolone, indolyl or 1,2,5-thiadiazolyl; and pharmaceutically acceptable salts thereof.

Further preferred are the above compounds of formula I wherein Ar represents 1-naphthyl, 1(2H)-oxo-3,4-dihydronaphth-5-yl, 5,6,7,8-tetrahydro-cis-6,7-dihydroxynaphth-1-yl, 4-indolyl, 3,4-dihydro-2(1H)-quinolon-5-yl, 3-cyano-2-pyridyl, 4-(4-morpholinyl)-1,2,5-thiadiazol-3-yl; and pharmaceutically acceptable salts thereof.

Particularly preferred are compounds of formula I wherein Ar represents phenyl or phenyl substituted by one to three members selected from lower (alkyl, alkenyl, alkynyl, alkanoyl, mono- or di-alkylamino, alkanoylamino, alkylsulfonylamino, alkoxycarbonyl, alkylcarbamoyl, alkylsulfamoyl, alkoxy, alkylthio, alkylsulfinyl, alkylsulfonyl, alkenyloxy and alkynyloxy), hydroxy, cyano, halo, pyrrolyl, amino, 5 to 7-membered (alkylene, oxalkylene, thiaalkylene)imino, benzyloxy, phenyl, 5 to 7-membered cycloalkyl, carbamoyl, sulfamoyl, and from 3 to 7-membered cycloalkyl-, phenyl-, hydroxy-, lower alkoxy-, lower alkoxycarbonylamino-, lower alkylthio-, lower alkylsulfinyl-, lower alkylsulfonyl- and carbamoyl-substituted (lower alkyl and lower alkoxy); R represents hydrogen, lower alkanoyl or aroyl; $R_1$ and $R_2$ represent hydrogen or lower alkyl;- or $R_1$ and $R_2$ combined represent alkylene of 2 to 5 carbon atoms; $R_3$ and $R_4$ represent hydrogen or lower alkyl; and X represents O or S; and pharmaceutically acceptable salts thereof.

Especially preferred are the above-cited compounds of formula I wherein R represents hydrogen; $R_1$ and $R_2$ are combined to represent alkylene of 2 to 4 carbon atoms to form a 5-, 6-, or 7-membered ring; $R_3$ and $R_4$ represent hydrogen or lower alkyl; and X represents O or S.

Highly preferred are the compounds of the formula II

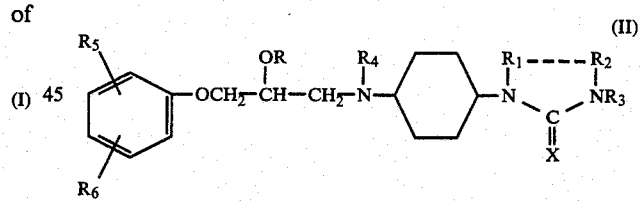

wherein R represents hydrogen or lower alkanoyl; $R_1$ and $R_2$ represent hydrogen; or $R_1$ and $R_2$ combined represent unbranched alkylene of 2 to 4 carbon atoms; $R_3$ and $R_4$ independently represent hydrogen or lower alkyl; each of $R_5$ and $R_6$ independently represents hydrogen, lower (alkyl, alkenyl, or alkynyl), lower (alkoxy, alkenyloxy or alkynyloxy), hydroxy, cyano, halo, amino, lower (mono- or di- alkylamino, alkanoylamino or alkylsulfonylamino), lower alkyl-(thio, sulfinyl or sulfonyl), morpholino, 1- or 2-pyrrolyl, phenyl, 5 to 7-membered cycloalkyl, lower alkanoyl, lower alkoxycarbonyl, carbamoyl, or sulfamoyl; $R_6$ also represents lower (alkyl or alkoxy) substituted by a member selected from cycloalkyl of 3 to 6 carbon atoms, from phenyl, from lower alkoxy, from hydroxy, from lower alkoxycarbonylamino, from lower alkyl-(thio, sulfinyl and sulfonyl), and from carbamoyl; X represents O or S; and pharmaceutically acceptable salts thereof.

Preferred in turn are the compounds of formula II wherein $R_3$ and $R_4$ represent hydrogen; $R_5$ represents hydrogen; $R_6$ represents lower alkyl, lower alkenyl, lower alkynyl, lower alkyl (thio, sulfinyl or sulfonyl), lower alkoxy, lower alkenyloxy, lower alkynyloxy, cyano, lower alkoxycarbonyl, carbamoyl, lower alkanoylamino, morpholino, pyrrolyl, 5 to 7-membered cycloalkyl; $R_6$ also represents lower (alkyl or alkoxy) substituted by cycloalkyl of 3 to 5 carbon atoms, by phenyl, by lower alkoxy or by carbamoyl; X represents O; and the pharmaceutically acceptable addition salts thereof.

Further preferred are the compounds of formula III

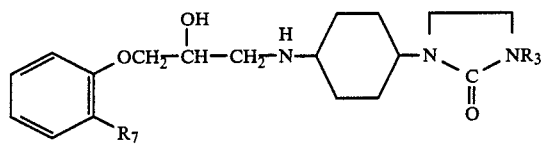

(III)

wherein $R_3$ represents hydrogen or lower alkyl; $R_7$ represents cyano, lower alkoxycarbonyl, pyrrolyl, morpholino, alkenyloxy of 3 to 6 carbon atoms, alkynyloxy of 3 to 6 carbon atoms, or alkoxy of 1 to 3 carbon atoms substituted by cyclopropyl; and pharmaceutically acceptable salts thereof.

The compounds of formulae I, II and III exist in isomeric forms wherein the two groupings on the cyclohexane ring (the two 1,4-cyclohexylene substituents) are either cis or trans to each other. Furthermore the asymmetric carbon atom bearing the OR group (hydroxy, alkanoyloxy or aroyloxy) in compounds of the invention may exist either in the S or R configuration. Thus the compounds of the invention exist in the form of stereoisomers e.g., geometric isomers, racemates, pure enantiomers or mixtures thereof, all of which are within the scope of the invention.

Preferred are the compounds of the invention, e.g., those of formulae I, II or III wherein the two 1,4-cyclohexylene substituents are cis to each other. Further preferred are the enantiomers wherein the carbon bearing the hydroxy, alkanoyloxy or aroyloxy group is in the S-configuration.

Of greatest interest are the compounds of formula III, wherein $R_3$ represents hydrogen, $R_7$ represents allyloxy, propargyloxy or cyclopropylmethoxy; the stereoisomers and enantiomers thereof; and pharmaceutically acceptable acid addition salts thereof. In turn, the cis stereoisomers and S enantiomers are preferred.

The general definitions used herein have the following meanings within the scope of the present invention.

An aromatic radical represents preferably phenyl, naphthyl, pyridyl, quinolyl, isoquinolyl, indolyl and 1,2,5-thiadiazolyl. A partially hydrogenated bicyclic carbocyclic or heterocyclic aromatic radical is preferably tetrahydronaphthyl, tetrahydroquinolyl or tetrahydroisoquinolyl. The optional substituents on phenyl and the phenylene portion of the above cited bicyclic radicals are preferably lower alkoxy, e.g. methoxy; lower alkyl, e.g. methyl; halogen, e.g. chloro; hydroxy; and trifluoromethyl. The optional substituents on the heterocyclic or partially hydrogenated ring of bicyclic radicals include preferably lower alkoxy, lower alkyl, halogen, hydroxy, cyano, carbamoyl, substituted amino, (alkylene, oxalkylene and thiaalkylene)imino such as morpholino, and oxo in the case of the above-cited partially hydrogenated bicyclic radicals.

An alkenyl group, as such or as present in e.g. alkenyloxy, represents straight chain or branched alkenyl preferably up to 7 carbon atoms, e.g., 2-propenyl (allyl), 2-butenyl, 2-methyl-2-propenyl, 2-methyl-2-butenyl and the like.

An alkynyl group, as such or present in e.g. alkynyloxy, represents straight chain or branched alkynyl preferably up to 7 carbon atoms, e.g., 2-propynyl (propargyl), 2-butynyl, 2-pentynyl and the like.

The term "lower" referred to above and hereinafter in connection with organic radicals or compounds respectively defines such with up to and including 7, preferably up and including 4 and advantageously one or two carbon atoms.

A lower alkyl group preferably contains 1-4 carbon atoms and represents for example ethyl, propyl, butyl or advantageously methyl.

A lower alkoxycarbonyl group preferably contains 1-4 carbon atoms in the alkoxy portion and represents, for example, methoxycarbonyl, propoxycarbonyl, isopropoxycarbonyl or advantageously ethoxycarbonyl.

A lower alkylene group may be branched or unbranched, preferably contains 1 to 7 carbon atoms, and represents advantageously 1,2-ethylene, 1,3-propylene, 1,4-butylene, 1,5-pentylene and the like.

Cycloalkyl represents preferably cyclopropyl, cyclopentyl, cyclohexyl, and cycloheptyl. Oxalkyleneimino represents preferably morpholino; thiaalkyleneimino represents preferably thiomorpholino; lower alkyleneimino preferably represents pyrrolidino or piperidino.

Aroyl is preferably benzoyl; benzoyl substituted by one to three of lower alkyl, lower alkoxy, halo or trifluoromethyl; or heteroaroyl, e.g., nicotinoyl.

Lower alkanoyl is preferably acetyl, propionyl or butyryl.

Lower alkoxy is preferably ethoxy, propoxy, isopropoxy or advantageously methoxy.

Lower alkylthio is preferably ethylthio, propylthio or advantageously methylthio.

Lower alkylsulfinyl is preferably ethylsulfinyl, propylsulfinyl, advantageously methylsulfinyl.

Lower alkylsulfonyl is preferably ethylsulfonyl, propylsulfonyl, advantageously methylsulfonyl.

Lower alkoxycarbonylamino is preferably ethoxycarbonylamino, methoxycarbonylamino.

Halo is preferably fluoro or chloro, but may also be bromo or iodo.

Alkylamino is preferably mono- or di-(methyl, ethyl, propyl)amino.

Alkylcarbamoyl is preferably mono- or di-N-(methyl, ethyl, propyl) carbamoyl.

Alkylsulfamoyl is preferably mono- or di-N-(methyl, ethyl, propyl)-sulfamoyl.

Alkanoylamino is preferably acetylamino, propionylamino.

Alkylsulfonylamino is preferably methylsulfonylamino, ethylsulfonylamino.

Pharmaceutically acceptable salts are acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

In addition to the pharmaceutically acceptable salts cited above, any prodrug derivatives, e.g., pharmaceutically acceptable esters of the alcohols (compounds of formula I wherein R is hydrogen) of this invention that may be convertible by solvolysis or under physiological conditions to said alcohols, represent a further object of this invention.

Such esters are preferably straight chain or branched lower alkanoyl esters, e.g., the acetyl, isobutyryl ester; aroyl esters, e.g., the benzoyl, nicotinoyl ester; carbamoyl esters, (carbamates), e.g. the N-ethylcarbamoyl, N-methylcarbamoyl ester.

The compounds of this invention exhibit valuable pharmacological properties, primarily cardiovascular, e.g., antihypertensive and cardiac effects, by inter alia inhibiting $\beta$-adrenergic receptors. This inhibitory action is attributed to the strong affinity of the compounds of this invention for $\beta$-adrenergic receptors. For compounds of this invention, having no or only slight inherent $\beta$-stimulating activity, this $\beta$-receptor adrenergic receptor affinity results in potent adrenergic blocking activity. In addition, the compounds of this invention exhibit $\alpha$-adrenergic blocking properties which may also contribute to e.g. their antihypertensive effect, but they are substantially free of liability to cause orthostatic hypotension.

The above-cited properties are demonstrable by in vitro or in vivo tests, using advantageously mammals, e.g., rats, cats, dogs or isolated organs thereof, as test objects. The animals may either be normotensive or hypertensive, e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starch suspensions or aqueous solutions respectively. The applied dosage may range between about 0.01 and 100 mg/kg/day, preferably between about 0.05 and 50 mg/kg/day, advantageously between about 0.1 and 30 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, representative members of the compounds of this invention, illustrated by the examples herein, are very effective in hypertensive rats and dogs at p.o.-doses as low or lower than 10 mg/kg/day.

Thus the antihypertensive effect and reduction in heart rate are demonstrable in spontaneous hypertensive rats by indirect measurement of systolic pressure by sphygmomanometry of the rat's tail. Conscious rats are placed individually in restraint cages within a gently warmed chamber. After obtaining control values of blood pressure and heart rate, test compounds are administered orally once daily for 2 or 4 consecutive days. Blood pressure measurements are usualy made 24 hours after the first dose and at 2.0, 4.0 and 24 hours after each daily dosing thereafter, and responses are compared to those of rats dosed with the treatment vehicle.

Illustrative of the compounds of this invention, the compounds of Examples 1, 2 and 3 m demonstrate a significant antihypertensive and heart rate reducing (bradycardic) effect when administered to spontaneous hypertensive rats at an oral dose as low as 10 mg/kg or even lower.

The antihypertensive and bradycardic effects are also measured in conscious chronically hypertensive dogs, the hypertension being produced by impairment of renal function. Arterial pressure is measured by direct percutaneous femoral artery puncture using a needle connected to a transducer. After collecting control data, dogs are treated orally once daily for 4 days with capsules containing the test compound. Blood pressure and heart rate measurements are made at 1.5, 3, 6 and 24 hours after each daily dosing, and the results are compared to pre-treatment control values.

Illustrative of the invention, the compounds of e.g., Examples 1 and 3 m at a dose of 10 mg/kg p.o. produce a sustained reduction in mean arterial pressure and lower the heart rate in the renal hypertensive dog.

The $\beta$-adrenergic receptor binding properties indicative of the $\beta$-adrenergic regulatory, e.g., blocking activity of said new compounds, are determined in the $\beta$-receptor binding assay in vitro by a modification of the procedure described in Life Sciences 17, 993 (1975).

$^3$H-Dihydroalprenolol binds specifically to brain membrane preparations and such binding is inhibited by known $\beta$-adrenergic receptor agonists and antagonists.

In the binding assay, 2 ml aliquots of the suspension of a membrane preparation (equivalent to ca. 20 mg of calf brain caudate nuclei) are added to ice-cooled tubes containing $^3$H-dihydroalprenolol with or without test compound freshly dissolved in 0.1% ascorbic acid. The final concentration of $^3$H-dihydroalprenolol is 1.0 nM. Test compounds are assayed over a wide range of concentrations. Tubes are incubated at 37° C. for 10 minutes and the suspensions are immediately filtered under vacuum through glass fiber filters. The filters are washed with 15 ml of cold 50 mM Tris-HCl (pH 7.9 at 25° C.), placed in scintillation vials with 12 ml of scintillation solution, first shaking for 90 minutes, and then counted for radioactivity.

The IC$_{50}$ values (concentrations of test compounds required to inhibit the specific binding of 1.0 nM $^3$H-dihydroalprenolol by 50%) are determined graphically.

The compounds of the invention inhibit dihydroalprenolol $\beta$-receptor binding with IC$_{50}$ values as low as 5 nM (5×10$^{-9}$M) or lower. Illustrative of the inventions, e.g., the compounds of examples 1, 2a, 3b, and 3i have an IC$_{50}$ of about 80, 5, 50 and 4 nM respectively.

The $\beta$-adrenergic receptor antagonist activity of the compounds of this invention can be demonstrated in vitro by antagonism of the epinephrine activation of an adenylate cyclase preparation from guinea pig cerebellum (J. Neurochemistry 22, 1031, 1974). Illustrative of the compounds of this invention, e.g. the compounds of examples 1, 2a, 3b demonstrate an IC$_{50}$ of about 3 to 5 nM (3–5×10$^{-9}$M), indicative of potent $\beta$-adrenergic blocking activity, in the above $\beta$-adrenergic receptor antagonist assay.

The $\alpha$-adrenergic receptor binding properties indicative of $\alpha$-receptor blocking properties are demonstrated e.g., in vitro by inhibition of the binding of the known $\alpha$-blocker prazocin ($^3$H-prazocin) to a synaptosomal membrane preparation from rat forebrain (Naunyn-Schmiedebergs Arch. Pharmacol. 308, 223, 1979).

Illustrative of the invention, compounds of e.g. examples 1, 2a, 3b and 3m are active in the above α-receptor binding assay with $IC_{50}$ values near 1 μM ($1\times10^{-6}$M).

Indicative of the antiglaucoma effect of the compounds of the invention is the intraocular pressure-lowering effect demonstrable in mammals e.g. in normotensive rabbits essentially according to the methodology described by D. E. Potter and J. M. Rowland in Experimental Eye Research 27, 615–625, 1978. The intraocular pressure-lowering effect is determined as follows:

$2\times50$ μl portions of a solution of the test compound in sterile water at various concentrations are applied to one eye of male, albino New Zealand rabbits weighing 3-4 kg, and $2\times50$ μl of the vehicle is applied to the contralateral eye serving as control. The intraocular pressure (in mm Hg) in each eye is measured tonometrically just before treatment and then at 1,2 and 3 hour intervals after administration. The difference between the intraocular pressure of the treated and control eye is determined.

Illustrative of the compounds of the invention, the compounds of Examples 1 and 2a significantly lower the intraocular pressure in the rabbit at a concentration of about 20 nM and 6.4 nM respectively.

Accordingly, the compounds of the invention are useful in mammals as α- and β-adrenergic blockers, and as cardiovascular agents, especially antihypertensive and heart rate lowering agents, for example, in the treatment, management and prevention of cardiovascular conditions such as hypertension, as well as cardiac disorders such as myocardial infarction, arrhythmia and angina, and/or other conditions responsive to inter alia β-adrenergic blockade, such as tension or anxiety, glaucoma and migraine. They are also useful intermediates in the preparation of other valuable products, especially of pharmacologically active compositions.

The present invention also relates to the methods for the preparation of the compounds of formula I. Unless specified otherwise hereafter, the symbols Ar, R, $R_1$ to $R_4$, and X are understood to have the meaning as previously defined for the compounds of formula I.

The compounds of this invention are prepared according to the following processes, comprising:

(a) condensing a compound of the formula IV

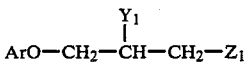

with a compound of the formula V

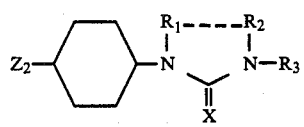

in which one of the groups $Z_1$ and $Z_2$ represents a reactive esterified hydroxy group and the other represents the group $NHR_4$, and $Y_1$ represents hydroxy, alkanoyloxy or aroyloxy; or in which $Y_1$ and $Z_1$ together represent the epoxy group, $Z_2$ represents the amino group $NHR_4$, and Ar, $R_1$, $R_2$, $R_3$, $R_4$ and X have the meanings given above; and (b) if desired, converting a compound which may be thus obtained into a different compound of the formula I; and/or (c) if desired, converting a resulting free compound into a salt or a resulting salt into a free compound; and/or (d) if desired, separating a resulting isomeric mixture into its isomers or a resulting racemate into its antipodes.

A reactive esterified hydroxy group $Z_1$ or $Z_2$ is hydroxy group esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example phenylsulfonyloxy or 4-methylphenylsulfonyloxy (tosyloxy).

The above reaction is carried out in a manner known per se usually in the presence of a solvent or mixture of solvents, and, if necessary, whilst cooling or heating, for example at a temperature range of from approximately $-20°$ C. to approximately $150°$ C., in an open or closed vessel and/or in an inert gas atmosphere, for example a nitrogen atmosphere. When using a starting material having a reactive esterified hydroxy group, the reaction is carried out advantageously in the presence of a basic medium, such as an inorganic base, for example an alkali metal or alkaline earth metal carbonate or hydroxide, or in the presence of an organic basic medium, such as an alkali metal lower alkanolate, and/or an excess of the basic reactant.

More particularly the compounds of formula I are prepared by condensation of an oxirane of formula VI

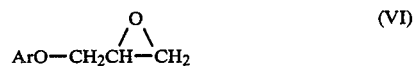

with an amine of formula VII,

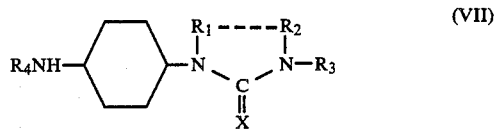

or a stereoisomer thereof, wherein $R_1$ and $R_2$ represent independently hydrogen or lower alkyl; or $R_1$ and $R_2$ combined represent unbranched or branched alkylene of 2 to 7 carbon atoms separating the two nitrogen atoms thereto attached by 2 to 4 carbon atoms; $R_3$ and $R_4$ independently are hydrogen or lower alkyl; and X represents oxo or thio.

Preferred intermediates of formula VII are represented by compounds of formula VIII

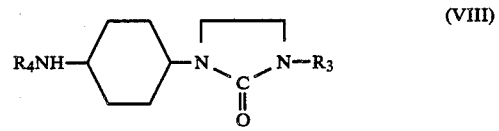

or the stereoisomers thereof, advantageously the cis isomers, wherein $R_3$ and $R_4$ are hydrogen or lower alkyl. The starting materials of the formula IV (and e.g. VI) are known in the literature or can be prepared in a manner known per se, e.g. as illustrated in the examples herein. For instance, racemic or optically active starting materials of formula IV are prepared by first condensing compounds of the formula ArOH or an alkali metal derivative thereof with e.g. racemic or optically active epichlorohydrin or benzyl 2,3-epoxypropyl ether, and subsequently hydrogenolyzing, acylating and/or cyclizing the resulting products.

The starting materials of formula VII or VIII (compounds of formula V wherein $Z_2$=$NHR_4$) are preferably prepared by e.g. hydrogenation of the compounds of formula IX

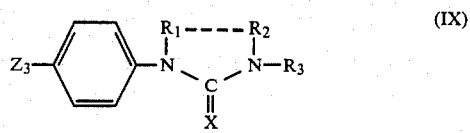
(IX)

wherein $Z_3$ represents $R_4NH$, nitro or acyl-$NHR_4$; $R_1$, $R_2$, $R_3$, $R_4$ and X have meaning as previously defined; Acyl-$NHR_4$ represents acylated $NHR_4$ e.g. (alkoxycarbonyl- or aralkoxycarbonyl- such as t-butyloxycarbonyl-, carbobenzoxy-; lower alkanoyl- such as acetyl-, trifluoroacetyl-) substituted $NHR_4$.

The hydrogenation of the compounds of formula IX is performed by methods known per se, preferably with catalytically activated hydrogen, such as hydrogen in the presence of e.g., platinum, palladium, nickel, advantageously rhodium catalyst in a solvent such as water, acetic acid, ethanol, at room or elevated temperature, and at atmospheric or superatmospheric pressure, e.g., at 3 atm. pressure.

The resulting compounds obtained by hydrogenation of the compounds of formula IX wherein $Z_2$ represents acyl-$NHR_4$ are converted to compounds of formula VII (compounds of formula V wherein $Z_2$ represents $NHR_4$) by removal of the acyl protecting group, e.g., by hydrolysis with aqueous base such as sodium hydroxide, or aqueous acid such as hydrochloric acid, or by hydrogenolysis with hydrogen in presence of a catalyst such as palladium.

Furthermore, the resulting intermediates of formula VII or VIII wherein $R_4$ is hydrogen may be converted to the intermediates of formula VII or VIII wherein $R_4$ is lower alkyl e.g. by alkylation with a reactive esterified lower alkanol such as a lower alkyl halide or under conditions of reductive alkylation, e.g. with formaldehyde in the presence of formic acid, or with acetone in the presence of sodium cyanoborohydride, and the like.

The intermediates of formula V, VII or VIII may be obtained as cis or trans isomers or as a mixture thereof. If a mixture of cis and trans isomers is obtained the isomers may be separated by methods known to the art, e.g. chromatography, crystallization and the like. Advantageously, the cis isomers of the amines of formula VII or VIII leading to the preferred compounds of the invention are isolated, either as free bases or acid-addition salts.

A further possible procedure for the preparation of compounds of formula I consists of condensing a compound of the formula ArOH, preferably in the form of a metal salt, e.g. an alkali metal derivative thereof, with a compound of the formula X,

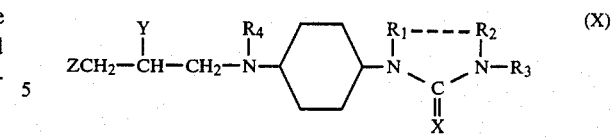
(X)

wherein Z is reactive esterified hydroxy and Y represents OR; or Z and Y together form a epoxy group; and wherein Ar, R, $R_1$, $R_2$, $R_3$, $R_4$ and X are as previously defined; and wherein the amino, hydroxy and other functional groups may optionally be in protected form; or with a compound of the formula XI

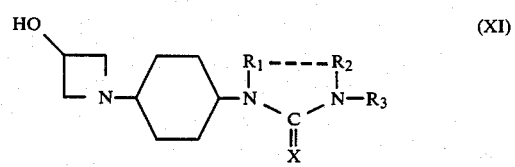
(XI)

wherein $R_1$-$R_3$ and X are as previously defined and in which hydroxy may be in optionally protected form; and, if desired, converting the resulting compound to another compound of the invention.

The above condensations may be carried out under conditions known per se and advantageously in an inert solvent at room or elevated temperature and preferably in an inert atmosphere.

Intermediates of formula XI may be obtained by cyclization of an intermediate of formula X wherein Z represents reactive sterified hydroxy, Y represents hydroxy and $R_4$ represents hydrogen. Intermediates of formula X may be prepared by condensing the amines of formula VII with e.g. epichlorohydrin.

A further possible process for the preparation of compounds of formula I consists of the reduction of a compound of formula XII,

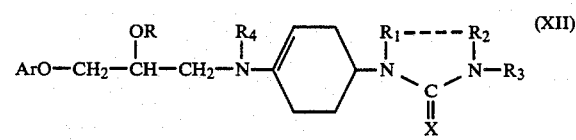
(XII)

or a tautomer thereof if $R_4$ represents hydrogen, wherein Ar, R, $R_1$, $R_2$, $R_3$, $R_4$ and X have meaning as previously described to yield a compound of formula I.

The reduction may be carried out either by catalytic hydrogenation, e.g., with hydrogen in the presence of Raney nickel catalyst or with a reducing agent, such as sodium cyanoborohydride, the reaction being carried out by well-known procedures in the art, e.g. in a solvent, such as ethanol, preferably at ambient or slightly elevated temperature.

Intermediates of formula XII, wherein R represents hydrogen may exist in isomeric form represented by formula XIIa.

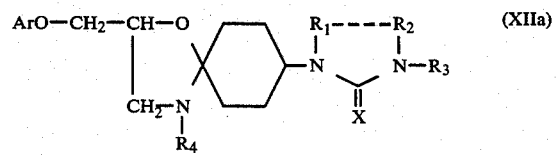
(XIIa)

The intermediates of formula XII and XIIa may be prepared, e.g. in situ, by condensation of an amine of formula XIII

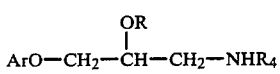

with a ketone of formula XIV,

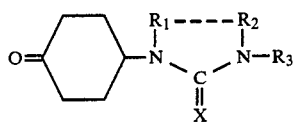

such condensation may occur either spontaneously or preferably in the presence of a dehydrating agent, e.g. boron trifluoride, magnesium sulfate or molecular sieves.

The starting amines of formula XIII are obtainable by condensation of a compound of formula VI with $R_4NH_2$ under standard aminolysis conditions. Ketones of formula XIV may in turn be prepared by oxidation of compounds of formula VII with e.g., an alkali metal hypochlorite, preferably under conditions of phase transfer catalysis, as described in Tetrahedron Letters 1976, 1641.

Futhermore, compounds of the instant invention may be prepared by reducing a compound of formula XV

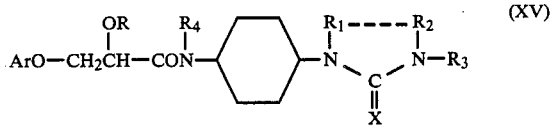

with e.g. simple or complex light metal hydrides, e.g. alane, borane or lithium aluminum hydride according to procedures well-known to the art.

Intermediates of formula XV may in turn be prepared by condensation of an acid of formula XVI, optionally in protected form when R represents hydrogen,

or a reactive functional derivative thereof, e.g. an acid chloride or a mixed anhydride, with an amine of formula VII, according to well-known procedures for the preparation of amides.

Condensation of a free carboxylic acid of formula XVI with an amine of formula VII is preferably carried in the presence of a coupling reagent such as dicyclohexylcarbodiimides or 1,1′-carbonyldiimidazole, according to procedures well known in the art.

Condensation of a reactive functional derivative of a compound of formula XVI with an amine of formula VII occurs spontaneously, or in the presence of bases such as potassium carbonate, pyridine or triethylamine, in an inert solvent, such as methylene chloride, at ambient or elevated temperature.

The acids of formula XVI may be prepared essentially by the procedures described in U.S. Pat. No. 3,699,097 e.g. by condensation of ArOH with chlorolactic acid in aqueous sodium hydroxide solution.

In addition, compounds of this invention may be prepared by reduction of a compound of formula XVII,

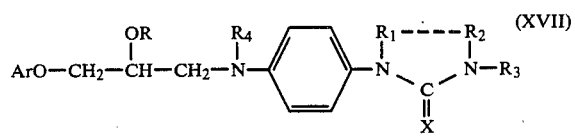

advantageously, by e.g. selective catalytic hydrogenation with hydrogen in the presence of a catalyst, such as nickel, rhodium or platinum, preferably in an acidic medium such as acetic acid or ethanol in the presence of a mineral acid. Said reduction is most useful when Ar represents a group that is relatively resistant to hydrogenation conditions.

The starting materials XVII may be prepared by condensation of a compound of formula IV with a compound of formula IX wherein $Z_3$ represents $R_4NH$, under condensation conditions similar to those described for the condensation of compounds of formula IV with compounds of formula V wherein $Z_2$ represents $NHR_4$.

The compounds of the invention obtained by any of the methods described above can be converted into each other according to conventional methods known to the art, and e.g. as illustrated herein.

For example, compounds of formula I, wherein R represents alkanoyl or aroyl, may be converted to compounds of formula I wherein R represents hydrogen by hydrolysis with e.g. aqueous acid, such as hydrochloric acid, or with aqueous alkali, such as lithium or sodium hydroxide.

Conversely, the conversion of compounds of formula I wherein R represents hydrogen, to compounds of formula I wherein R represents alkanoyl or aroyl may be carried out by condensation with a corresponding carboxylic acid, or reactive derivative thereof, according to esterification procedures well known to the art, advantageously under non-basic conditions.

Futhermore, compounds of formula I wherein $R_4$ represents hydrogen, may be converted to the compound of formula I wherein $R_4$ represents lower alkyl, by reaction with a reactive esterified lower alkanol, e.g. with a lower alkyl halide, thereby preferably isolating the resulting compound of formula I as the corresponding acid-addition salt, or by reductive alkylation, e.g. with formaldehyde and formic acid to yield the compound of formula I wheein $R_4$ represents methyl.

Compounds of formula I, optionally in protected form, wherein $R_3$ represents hydrogen may be converted to compounds wherein $R_3$ represents lower alkyl by condensation with a reactive derivative of a lower alkanol, e.g. with a lower alkyl iodide, in the presence of a strong base, e.g. sodium hydride in an inert solvent such as dimethylformamide.

Unsaturated compounds, such as those bearing an alkenyl or alkynyl radical, may also be hydrogenated with catalytically activated hydrogen to obtain compounds of formula I or intermediates bearing the corresponding alkyl radical.

Also compounds of formula I or intermediates optionally in protected form, wherein X represents O may be converted to compounds wherein X represents S by sulfurating agents, e.g., phosphorous pentasulfide.

With reference to the above reactions, the expression "in protected form" is understood to mean appropriately protecting the potentially reactive, e.g. amino, hydroxy and other interfering substituents in accordance with protective techniques well known to the art, e.g. as illustrated below, such that interfering reactions are avoided, by protecting such substituents prior to the desired reaction and subsequently, if necessary, removing the protective groups to obtain the desired compounds, e.g. of formula I.

Thus where OR represents hydroxy or the Ar moiety contains a free hydroxy group, such hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

Similarly, a free basic amino group, the group $-NR_4-$ bearing at least one hydrogen on nitrogen, may be protected in the form of easily cleaved amides, e.g. as an acyl derivative such as the benzyloxycarbonyl (carbobenzyloxy) or the t-butyloxycarbonyl derivatives, or any other easily removable N-protecting group as commonly used in peptide chemistry.

In a resulting protected compound of formula I or intermediate, in which one or more of the functional groups are protected, the protected functional groups, e.g. the amino and/or hydroxy groups can be liberated, in a manner, known per se, e.g. by means of solvolysis, especially hydrolysis with acid, or by means of reduction, especially hydrogenolysis.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Whenever desirable, the above processes are carried out after first suitably protecting any potentially interfering reactive functional groups, as illustrated above and in the example herein.

Advantageously, those starting materials should be used in said reactions, that lead to the formation of those compounds indicated above as being especially preferred. The preferred starting materials of formula VII or VIII are the cis isomers thereof.

The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers such as antipodes, or as mixtures of optical isomers such as racemates, or as mixtures of geometric isomers.

In case geometric or diastereomeric mixtures of the above compounds or intermediates are obtained, these can be separated into the single racemic or optically active isomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d- or l-(tartrate, mandelate, camphorsulfonate salts, or 1-naphthyl-1-ethylisocyanate condensation products) of compounds having a basic salt-forming group, or of d- or l-($\alpha$-methylbenzylamine, cinchonidine, cinchonine, quinine, quinidine, ephedrine, dehydroabietylamine, brucine or strychnine)-salts of compounds having an acidic salt-forming group.

Advantageously, the more active of the isomers and/or antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide or a basic salt, e.g., an alkali metal hydroxide or carbonate, or a cation exchange preparation. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for the crystallization.

The present invention additionally relates to the compounds of the formula I and their pharmaceutically acceptable, non-toxic acid addition salts for use as medicaments, especially as $\alpha$- and $\beta$- adrenergic blockers, e.g. as hypotensive, antihypertensive and cardioactive agents, for example for the treatment of elevated blood pressure, cardiac disorders, and other diseases responsive to adrenergic receptor blockade, and especially for their use for the preparation of pharmaceutical compositions, especially compositions having adrenergic receptor blocking activity, particularly antihypertensive and cardiac activity.

The pharmaceutical compositions according to the invention are those suitable for topical, such as ocular, enteral, such as oral or rectal, and parenteral administration to mammals, including man, for the treatment or prevention of diseases responsive to adrenergic receptor blockade e.g. glaucoma, cardiovascular diseases such as hypertension and cardiac disorders, comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable and ocular compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

More specifically, the invention relates advantageously to the method of treatment of cardiovascular diseases, especially hypertension, using the compounds of the formula I or pharmaceutically acceptable, non-toxic salts of such compounds as pharmacologically active substances, especially as anti-hypertensive agents, preferably in the form of above-cited pharmaceutical compositions. The dosage of active compound administered is dependent on the species of warm-blooded animal, the body weight, age and individual condition, and on the form of administration.

A unit dosage for a mammal of about 50 to 70 kg may contain between about 10 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

EXAMPLE 1

A mixture of 657.6 g of 92% pure o-(allyloxy)phenoxymethyloxirane (U.S. Pat. No. 3,483,221) and 512 g of cis-1-(4-aminocyclohexyl)-2-imidazolidinone is stirred and refluxed for 6 hours in 6,000 ml of isopropanol. To the above reaction mixture, while still hot, is added 162.1 g of fumaric acid. The resulting mixture is allowed to stir at room temperature overnight. The crude product is filtered and washed with 1000 ml of isopropyl alcohol. The thus obtained wet solid is first recrystallized from 5000 ml of isopropyl alcohol and then dried in a vacuum oven at 65° to constant weight to give a white crystalline product, m.p. 154°–155°. Recrystallization of 1781 g of the resulting salt from 9700 ml of anhydrous ethanol yields cis-1-{4-[3-(o-allyloxyphenoxy)-2-hydroxypropylamino]-cyclohexyl}-2-imidazolidinone hemifumarate salt, m.p. 156°–7°, being the cis compound of formula III wherein $R_3$ represents hydrogen and $R_7$ represents allyloxy, as the hemifumarate salt.

A solution of 1575 g of the above salt in 7875 ml of water is basified with a solution of 4.537 moles of potassium carbonate in 790 ml of water. The cis 1-{4-[3-(o-allyloxyphenoxy)-2-hydroxypropylamino]-cyclohexyl}-2-imidazolidinone is obtained as an oil. This is re-converted as described above to the hemifumarate salt of higher purity.

The starting material is prepared as follows:

A solution of 1800 g of p-aminoacetanilide in 7000 ml of dimethylformamide is stirred at room temperature. The solution is then cooled to 10°–15° in an ice-water bath. To the stirred cooled solution is added 1440 g of 2-chloroethyl isocyanate in a thin stream over a 50-minute period, keeping the reaction mixture temperature between 20° and 25°. The reaction mixture is stirred at room temperature for 90 minutes; 8000 ml of ice-water is added over a 20-minute period. After stirring for an additional 2 hours, the solid is filtered off and washed with 4000 ml of water. The crude product is slurried with 7000 ml of 95% alcohol. The solid is filtered off and air-dried overnight at room temperature to give 1-(p-acetamidophenyl)-3-(2-chloroethyl)-urea, m.p. 207°–9° dec.

A mixture of 1600 g of 1-(p-acetamidophenyl)-3-(2-chloroethyl) urea in 7200 ml of dimethylformamide is stirred at room temperature under an atmosphere of nitrogen. To the resulting solution is added a solution of 400 g of sodium methoxide in 2000 ml of methyl alcohol (anhydrous) in a thin stream over a 90-minute period. The temperature rises during the addition. The reaction mixture is stirred for an additional 20 minutes and then heated to 70°–75° and kept at this temperature for 1 hour. The reaction mixture is then allowed to cool slowly to 32° over a period of about 3 hours with stirring; 5000 ml of ice-water is then added rapidly. Stirring at room temperature is continued for 4 hours and the mixture is allowed to stand at room temperature overnight. The solid is filtered off and washed with 3000 ml of water and air-dried for about 2 days at room temperature to give 1-(p-acetamidophenyl)-2-imidazolidinone, m.p. 270°–273°.

A mixture of 4213 g of 1-(p-acetamidophenyl)-2-imidazolidinone in 39,000 ml of water and 2930 g of 5% rhodium on carbon 50% wet with water is hydrogenated at 40°. The hydrogenation mixture is filtered, and the filtrate is concentrated in vacuo to dryness. The resulting solid is air-dried and then powdered. The crude product is recrystallized from 12,000 ml of acetone to give 1-(4-acetamidocyclohexyl)-2-imidazolidinone, m.p. 211°–230° as a mixture of cis and trans isomers.

To a solution of 3271 g of sodium hydroxide in 33,000 ml of water is added 3271 g of 1-(4-acetamidocyclohexyl)-2-imidazolidinone. The mixture is stirred and refluxed for 4 hours. The reaction mixture is cooled to room temperature and 3271 g of sodium chloride is added with stirring. The reaction mixture is extracted a total of 10 times using a total volume of 93,000 ml of dichloromethane. The dichloromethane solution containing the product is concentrated in vacuo to a volume of about 5 liters. To this solution is added 300 g of magnesium sulfate, anhydrous. The mixture is stirred at room temperature for about 3 hours, filtered and the filtrate concentrated in vacuo to dryness. The resulting residue is dried in high vacuum to constant weight to give 1-(4-aminocyclohexyl)-2-imidazolidinone, as a mixture of isomers which crystallizes on standing at room temperature.

A mixture of 9500 ml of anhydrous ethyl alcohol and 2323 g of 1-(4-aminocyclohexyl)-2-imidazolidinone is heated with mixing to effect solution. The solution is cooled to room temperaure and 3200 ml of a saturated solution of anhydrous hydrogen chloride gas in ethyl acetate is added to pH 1. The temperature of the mixture rises to 60° and the product crystallizes. The mixture is cooled to 10°. The crude product is filtered off, washed with 3500 ml of anhydrous ethyl alcohol and dried at 50°–60° in vacuo for 2 days. The crude hydrochloride salt is recrystallized twice from anhydrous methanol-ethyl ether (ca 1:1) to give cis 1-(4-aminocyclohexyl)-2-imidazolidinone monohydrochloride, m.p. 327°–8°.

A solution of 630 g of the cis 1-(4-aminocyclohexyl)-2-imidazolidinone monohydrochloride and 155 g of sodium methoxide in 6000 ml of anhydrous methanol is stirred at room temperature under an atmosphere of nitrogen for about 24 hours. The reaction mixture is cooled in an ice bath and the sodium chloride filtered off. The methanol filtrate is concentrated to dryness in vacuo. The residue is dissolved in 1700 ml of dichloromethane with heating. The mixture is cooled in an ice bath and filtered through a hyflo filter; the filter cake is washed with 750 ml of dichloromethane. The dichloromethane filtrate is concentrated to dryness in vacuo. The resulting residue is dried in high vacuum to constant weight to give cis 1-(4-aminocyclohexyl)-2-imidazolidinone, m.p. 121°–3°.

EXAMPLE 2

(a) A solution of (S)-[o-(cyclopropylmethoxy)-phenoxy]methyloxirane (25.77 g) and cis 1-(4-aminocyclohexyl)-2-imidazolidinone (23.6 g of Example 1) in 300 ml isopropanol is stirred at reflux under nitrogen for 5½ hours. After standing at room temperature 16 hours, the solution is concentrated under reduced pressure. The residue is dissolved in 300 ml of ethyl acetate, acidified to pH 1 with a solution of hydrogen chloride gas in ethyl acetate. An amorphous solid precipitates. The solid is filtered off and washed with ethyl acetate. The solid is dissolved in warm water, the solution is cooled to room temperature, washed with ethyl acetate (2×100 ml), basified with excess 10% aqueous sodium carbonate and extracted with ethyl acetate (2×200 ml). The organic extract is washed with 10% aqueous sodium carbonate and water (2×150 ml). The organic layer is dried over anhydrous sodium sulfate and concentrated under reduced pressure. The residue is dried under high vacuum briefly leaving crude product as a viscous oil.

The oil is converted to the hemi-fumarate salt by dissolving 40.86 g of the oil in 350 ml hot isopropanol and adding fumaric acid (5.3 g). The solution is cooled slowly to room temperature as the product crystallizes. The mixture is cooled further in an ice bath, the solid is filtered off and washed with cold isopropanol. The solid is dried in high vacuum at 50°, yielding the crude hemifumarate salt which is purified by treatment with ethyl alcohol, the chiral product being more soluble than the racemate. Repeated crystallization and removal of the more insoluble racemate by filtration permits isolation of (S)-cis-1-{4-[3-(o-cyclopropylmethoxyphenoxy)-2-hydroxypropylamino]-cyclohexyl}-2-imidazolidinone hemifumarate (salt of the S-enantiomer) on evaporation of the filtrates; m.p. 147°–149°, $[\alpha]_D^{25} = -8.41°$ (c=1.35, MeOH), representing a salt of the cis-(S)- compound of formula III wherein $R_7$ is cyclopropylmethoxy and $R_3$ is hydrogen.

The chiral purity is determined by NMR in the presence of a chiral shift reagent to be >95%.

(b) Similarly condensation of the (R)-[o-(cyclopropylmethoxy)phenoxy]methyloxirane (33.69 g) with cis-1-(4-aminocyclohexyl)-2-imidazolidinone yields the (R)-cis 1-{4-[3-(o-cyclopropylmethoxy)-2-hydroxypropylamino]-cyclohexyl}-2-imidazolidone hemifumarate (salt of the R enantiomer of the cis compound of formula III wherein $R_3$ is cyclopropylmethoxy), m.p. 150°–2° dec., $[\alpha]_D^{25} = +8.26°$ (c=1.36, MeOH).

The starting materials are prepared as follows:

A mixture of 42.5 g of (R)-epichlorohydrin, as described in J. Organic Chemistry 43, 4876 (1978), 36.8 g of o-(cyclopropylmethoxy)phenol in 164 ml acetone and 10ml hexane to which is added 30.9 g of powdered potassium carbonate is stirred at reflux in a nitrogen atmosphere for 42 hours. The mixture is cooled to room temperature, the solid collected and washed with acetone. The filtrate is carefully concentrated at room temperature under high vacuum. The residue is dissolved in ether (200 ml), washed with ice cold 1N sodium hydroxide (2×50 ml) and water (2×50 ml). After drying over anhydrous sodium sulfate, the solution is filtered and concentrated under reduced pressure. The residue is distilled in vacuo and the main fraction, b.p. 108°–121°/0.2 mm, is collected consisting of (S)-[-o-(cyclopropylmethoxy)-phenoxy]methyloxirane, $[\alpha]_D^{25} = +10.10°$ (C=2.4, MeOH).

Similarly prepared from (S)-epichlorohydrin is the (R)-[o-(cyclopropylmethoxy)phenoxy]methyloxirane, b.p. 120°–127°/0.2 mm Hg, $[\alpha]_D^{25} = -9.76°$ (c=1.58, MeOH).

The (S)-[-o-(cyclopropylmethoxy)-phenoxymethyl]oxirane is also prepared as follows:

A mixture of (S)-benzyl 2,3-epoxypropyl ether (8.95 g as described in Heterocycles Vol. 16, 381, 1981), o-cyclopropylmethoxyphenol (8.95 g) in 36 ml acetone and 4 ml hexane, to which is added powdered potassium carbonate (6.9 g), is stirred at reflux in nitrogen atmosphere for 74 hours. After cooling to room temperature the solid is filtered off and washed with acetone. The filtrate is concentrated under reduced pressure, the residue is dissolved in ether, the ether solution is washed 2x with water and dried over anhydrous sodium sulfate, filtered, and the filtrate is evaporated to dryness. The crude oil is distilled in vacuo, at 199°–212°/0.2 mm to yield (S)-1-benzyloxy-3-[o-(cyclopropylmethoxy)-phenoxy]-2-hydroxypropane.

A solution of (S)-1-benzyloxy-3-[o-(cyclopropylmethoxy)phenoxy]-2-hydroxypropane (10.97 g) in 100 ml ethanol, to which is added 3.5 g of 10% palladium on carbon, is hydrogenated at 45 lbs. pressure at room temperature until the uptake of hydrogen ceases (about 10 minutes). The catalyst is filtered off, washed with ethanol and the filtrate concentrated under reduced pressure leaving a crystalline residue that is recrystallized from 35 ml of ethanol; (S)-3-[o-(cyclopropylmethoxy)phenoxy]-1,2-propanediol, m.p. 95°–97°, $[\alpha]_D^{25} = 5.32°$ (c=0.99, $CH_3OH$) is obtained.

A solution of 3-[o-cyclopropylmethoxy)phenoxy]-1,2-propanediol (5.82 g) in 15 ml dry pyridine under a nitrogen atmosphere is cooled to 5° and p-toluenesulfonyl chloride (4.7 g) is added over 10 minutes with stirring. The mixture is stirred at 5° for 1½ hours, then left in the refrigerator at about 5° overnight. Ether (15 ml) is added and after standing an additional 1 hour at 5°, the solid is filtered off and washed with ether. The filtrate is evaporated to dryness at low temperature. The residue is taken up in ether, the solution is washed with ice cold water and then once with a saturated solution of sodium bicarbonate. After drying over anhydrous sodium sulfate, the solution is filtered and concentrated under reduced pressure and high vacuum to yield an oil, $[\alpha]_D^{25} = -8.49°$ (c=1.26, CH₃OH), being the (S)-3-[o-(cyclopropylmethoxy)phenoxy]-1,2-propanediol-1-tosylate.

To a solution of 3-[o-(cyclopropylmethoxy)phenoxy]-1,2-propanediol-1-tosylate (8.1 g) in 25 ml of methanol and 12 ml of ether, under a nitrogen atmosphere and cooled to 5°, is added while stirring 0.47 g of sodium in small pieces over 30 minutes. The mixture is stirred further at 5° for 2 hours. Carbon dioxide is bubbled into the mixture to adjust the pH to about 8. The mixture is filtered and the filtrate concentrated under reduced pressure in a warm water bath. Ether is added followed by ice water. The layers are separated, the organic layer is washed again with water, then dried over anhydrous sodium sulfate, and concentrated under reduced pressure. The resulting crude material is distilled in vacuo to give the (S)-[o-(cyclopropylmethoxy)phenoxy]methyloxirane identical to the product obtained in Example 2. The product crystallizes on standing at room temperature to form low melting waxy crystals.

EXAMPLE 3

Analogous to the methods described in the previous examples are prepared the following racemic compounds of formula II, wherein R, R₃, R₄ and R₅ are hydrogen, X is O; and R₁ and R₂ combined represent —CH₂CH₂—; all as the hemifumarate salts unless otherwise indicated.

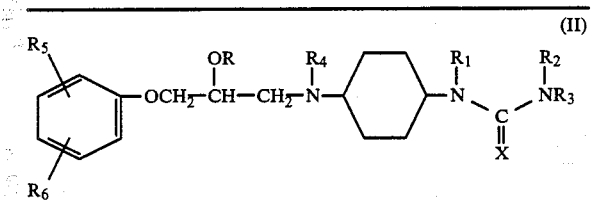

(II)

| Compound | R₆ | Isomer | Solvent of recrystallization | m.p. |
| --- | --- | --- | --- | --- |
| 3/a | o-OCH₃ | cis | iPrOH/CH₃OH | 190-2° |
| 3/b | o-propargyloxy | cis | 95% EtOH | 168° |
| 3/c | o-propargyloxy | trans | — | 92-8° |
| 3/d | m-propargyloxy | cis | EtOH | 177° |
| 3/e | p-propargyloxy | cis | iPrOH | 95-100° (iPrOH solvate) |
|  | (1:1 fumarate salt |  |  |  |
| 3/f | o-cyano | cis | EtOH | 192° dec. |
| 3/g | o-cyano | trans | EtOH | 215-6° |
| 3/h | o-(1-pyrrolyl) | cis | EtOH | 144° dec. |
| 3/i | o-(2-pyrrolyl) | cis | EtOH | 130-4° |
| 3/j | o-morpholino | cis | EtOH | 114-8° |
| 3/k | p-(2-methoxyethyl) | cis | iPrOH | 166-8° |
| 3/l | o-(cyclopropylmethoxy) | trans | iPrOH | 178-80° |
| 3/m | o-(cyclopropylmethoxy) | cis | EtoH | 168-170° |
| 3/n | o-benzyloxy | cis | EtOH | 141-6° |
| 3/o | o-CONH₂ | cis | — | 110° |
| 3/p | o-(2-methylpropoxy) | cis | acetone | 170-2° |
| 3/q | o-cyclohexyl | cis | iPrOH/acetone | 117-120° (hydrate) |
| 3/r | o-methoxycarbonyl | cis | iPrOH/acetone | 135-8° |
| 3/s | o-phenyl | cis | iPrOH | 146-8° |
| 3/t | p-benzyloxy (HCl salt) | cis | EtOH | 159-61° |
| 3/u | o-allyloxy | trans | EtOH | 149-50° |
| 3/v | o-allyl | cis | iPrOH/acetone | 158-9° |

The following known starting materials of formula VI are prepared as described in the readily available chemical literature.

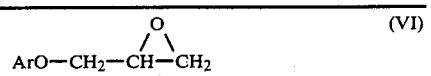

(VI)

| Ar | Ar |
| --- | --- |
| o-methoxyphenyl | p-benzyloxyphenyl |
| o-propargyloxyphenyl | p-(2-methoxyethyl)phenyl |
| m-propargyloxyphenyl | o-benzyloxyphenyl |
| p-propargyloxyphenyl | o-carbamoylphenyl |
| o-cyanophenyl | o-biphenyl |
| o-(1-pyrrolyl)phenyl | o-methoxycarbonylphenyl |
| o-(2-pyrrolyl)phenyl | o-allylphenyl |
| o-morpholinophenyl |  |

The following outer starting materials are prepared as follows:

(1) Catechol (110 g) is dissolved in 800 ml isopropanol. A solution of sodium hydroxide (41 g) in 45 ml water is added followed by cyclopropylmethyl chloride (155 g, 70% pure) and potassium iodide (5 g). The reaction mixture is stirred under nitrogen at reflux for 16 hours. The mixture is cooled to room temperature and the solid filtered off and washed with isopropanol. The filtrate is concentrated under reduced pressure, the brown residue dissolved in toluene (600 ml), 3 N hydrochloric acid added to acidify to pH 1 and the organic phase washed consecutively with water (4×100 ml), aqueous sodium bisulfite and water (3×100 ml). The organic layer is dried over anhydrous sodium sulfate, filtered through basic alumina (300 g) to remove any remaining catechol and concentrated under reduced pressure. The residue is distilled in vacuo through a Vigreaux column with reflux distilling head to give 2-(cyclopropylmethoxy)phenol, bp. 66°-68°/0.1 mm.

To a solution of 6.92 g of sodium hydroxide in 28 ml of water are added 200 ml of ethanol, 24.6 g 2-(cyclopropylmethoxy)phenol and 83.25 g of epichlorohydrin. The reaction mixture is stirred under N₂ for 24 hours at 25°, then allowed to stand for 36 hours. The mixture is filtered to remove NaCl and concentrated in vacuo. The residue is distributed between ether and water. The ether solution is washed an additional 3 times with water, dried and concentrated. The residue is distilled in vacuo. The fraction boiling between 133°-144° at 0.5 mm Hg corresponds to o-(cyclopropylmethoxy)phenoxymethyloxirane, the compound of formula VI in which Ar is o-(cyclopropylmethoxy)phenyl.

(2) Similarly prepared is o-(2-methylpropoxy)phenoxymethyloxirane, the compound of formula VI wherein Ar is o-(2-methylpropoxy)phenyl, b.p. 112°-122° at 0.3 mm Hg replacing cyclopropylmethyl chloride by 1-bromo-2-methylpropane in the above procedure.

(3) To a solution of 4.6 g of sodium hydroxide in 19 ml of water are added 150 ml of ethanol, 17.7 g of 2-cyclohexylphenol and 55.5 g of epichlorohydrin. The reaction mixture is stirred overnight, filtered and concentrated in vacuo. The residue is distilled in vacuo. The fraction boiling at 127°-133°/0.2 mm Hg corresponds to o-(cyclohexyl)phenoxymethyloxirane, the compound of formula VI wherein Ar is o-(cyclohexyl)phenyl.

(4) Trans 1-(4-aminocyclohexyl)-2-imidazolidinone hydrochloride is prepared as follows:

A solution of crude 1-(4-aminocyclohexyl)-2-imidazolidinone monohydrochloride (66 g), obtained by evaporation of the mother liquors from the preparation and purification of the cis 1-(4-aminocyclohexyl)-2- imidazolidinone hydrochloride of example 1 and which is composed of mostly trans isomer, is heated to boiling in a mixture of 1200 ml ethanol and 600 ml methanol. The insoluble material is filtered off (5.5 g, mainly cis isomer) and the hot filtrate cooled in an ice bath. The solid that crystallizes on cooling is filtered off and dried, yielding 9.1 g of a solid that is mainly the trans isomer, mp. 326°–328° dec. The solid is recrystallized by dissolving in 100 ml hot methanol and adding 100 ml ether. The solid that crystallizes on cooling to room temperature is collected and dried to yield trans 1-(4-aminocyclohexyl)-2-imidazolidone monohydrochloride, m.p. 328°–329° dec. The hydrochloride salt is converted to the free base, trans 1-(4-aminocyclohexyl)-2-imidazolidinone melting at 168°–170°.

EXAMPLE 4

Analogous to the procedure described in Examples 1 and 2, condensation of cis-1-(4-aminocyclohexyl)-3-methyl-2-imidazolidinone with o-(cyclopropylmethoxy)phenoxymethyloxirane (see Example 3) yields cis-1-{4-[3-(o-cyclopropylmethoxyphenyl)-2-hydroxypropylamino]-cyclohexyl}-3-methyl-2imidazolidinone hemifumarate salt, m.p. 145°–7°.

The starting material is prepared as follows:

p-Nitroaniline (40 g) in 200 ml dimethoxyethane is stirred under a nitrogen atmosphere and chloroethyl isocyanate (45.8 g) added in three portions over 4½ hours. The first portion of about 65% is added and the solution heated to reflux 1½ hours. Another 20% is then added, reflux is continued for 1½ hours, the rest of the isocyanate is added and reflux is continued for the final 1½ hours. The dark solution is cooled to room temperature, filtered and the filtrate concentrated under reduced pressure. Toluene is added to the residue and the mixture is concentrated again to remove unreacted chloroethyl isocyanate. The residue which essentially solidified is treated with ethyl acetate (400 ml) and water (200 ml) and the layers are separated. The organic layer is washed with water, dried over anhydrous sodium sulfate, filtered and concentrated under reduced pressure. A solution of the crude 1-(p-nitrophenyl)-3-(2-chloroethyl)urea in 300 ml methanol and 75 ml dimethylformamide is filtered and the filtrate is used directly in the next step.

The solution of the 1-(p-nitrophenyl)-3-(2-chloroethyl)urea (0.29 M) in 300 ml methanol and 75 ml dimethylformamide obtained above is stirred under nitrogen and a solution of sodium methoxide (prepared from 7.4 g Na, in 125 ml methanol) is added over a 20-minute period. The reaction mixture is refluxed 2 hours, cooled to room temperature, diluted with 300 ml of water and stirred. The precipitated solid is filtered off, washed with methanol/water (1:1, 150 ml) and then with water (100 ml). The solid is stirred in ethanol (150 ml) for a few minutes and filtered to give, after drying, 1-(p-nitrophenyl)-2-imidazolidinone, m.p. 243°–5°.

A solution of 1-(p-nitrophenyl)-2-imidazolidinone (25 g) in 450 ml of dimethylformamide is stirred under nitrogen and sodium hydride (50%, 6.4 g) added in small portions. The mixture is stirred at 50° for 1½ hours, cooled to room temperature, and then methyl iodide (25 g) is added. After stirring 2 hours, the pH of the reaction mixture is 9. Another batch of methyl iodide (4 g) is added over 6 hours until the pH of the mixture is about 8. Water (150 ml) is added, the precipitated solid is filtered off, washed with dimethylformamide/water (1:1), then with water (2×150 ml). The solid is dried to give 1-(p-nitrophenyl)-3-methyl-2-imidazolidinone, m.p. 207°–208°.

A solution of 1-(p-nitrophenyl)-3-methyl-2-imidazolidinone (12.45 g) in 150 ml glacial acetic acid, to which is added 6 g of 5% rhodium on alumina, is hydrogenated at 50° and 45 lbs. pressure. The catalyst is filtered off and the filtrate concentrated under reduced pressure. Water (25 ml) is added to the residue which is basified by addition of 50% aqueous sodium hydroxide while the mixture is cooled in an ice bath. Extraction with methylene chloride (5×70 ml), drying over anhydrous sodium sulfate, filtering and concentrating under reduced pressure gives crude 1-(4-aminocyclohexyl)-3-methyl-2-imidazolidinone. The oil is converted to the hydrochloride salt by dissolving in 100 ml isopropanol and adding a saturated solution of hydrogen chloride gas in ethyl acetate. Ether (50 ml) is added and the salt crystallizes on cooling to room temperature. Mixture is cooled further in the refrigerator. The solid is filtered off and dried to give cis 1-(4-aminocyclohexyl)-3-methyl-2-imidazolidinone hydrochloride, m.p. 287°–298°.

The hydrochloride salt is converted to the free base by dissolving 8.2 g of the salt in 50 ml water, adding 20 ml of 50% aqueous sodium hydroxide and extracting with methylene chloride (5×40 ml). The methylene chloride solution is dried over anhydrous sodium sulfate, filtered and concentrated to give cis 1-(4-aminocyclohexyl)-3-methyl-2-imidazolidinone, m.p. 81°–87°.

EXAMPLE 5

A mixture of cis-1-(4-[3-(o-allyloxyphenoxy)-2-hydroxypropylamino]-cyclohexyl)-2-imidazolidinone (4.4 g) in 15 ml isopropanol, 37.5% aqueous formaldehyde (0.671 g), and formic acid (2.6 g) is stirred at reflux for 19 hours. The solution is cooled to room temperature, 1 ml concentrated hydrochloric acid is added and the mixture concentrated to dryness. The glassy residue is dissolved in 100 ml of water, made alkaline with excess of 25% aqueous sodium hydroxide and extracted with methylene chloride (1×50 ml, 1×25 ml). The extract is dried, filtered and concentrated to give a residue which is purified by preparative thin layer chromatography on silica gel, using ethyl acetate-methanol-ammonium hydroxide (90:5:5) as the eluent, to yield the cis-1-{4-[3-(o-allyloxyphenoxy)-2-hydroxy-N-methylpropylamino]cyclohexyl}-2imidazolidinone as an oil. The hydrochloride salt, m.p. 80° dec., is prepared by dissolving 2.3 g of the base in 50 ml ethyl acetate, adding a saturated solution of hydrogen chloride gas in ethyl acetate, and collecting the resulting salt.

EXAMPLE 6

A mixture of 3.0 g of cis-1-(4-aminocyclohexyl)-2-imidazolidinone, 3.2 g of 3-chloro-4-(oxiranylmethyloxy)-1,2,5-thiadiazole and 40 ml of isopropanol is refluxed with stirring for 7 hours.

The reaction mixture is filtered, the filtrate is acidified with a solution of anhydrous HCl in ethyl acetate; the hydrochloride salt of the product precipitates as an amorphous solid. After cooling, the supernatant solution is decanted and the crude hydrochloride salt is dissolved in 50 ml of water. The solution is filtered, made basic by addition of 2 N NaOH and the free base extracted into methylene chloride. The methylene chloride solution is dried and concentrated in vacuo. A solution of the crude free base in 18 ml of isopropanol is heated to reflux and 0.27 g of fumaric acid added.

Crystallization of the product gives cis-1-{N-[3-(4-chloro-1,2,5-thiadiazol-3-yloxy)-2-hydroxy-propylamino]cyclohexyl}-2-imidazolidinone hemifumarate m.p. 163°; solvent for recrystallization is isopropanol.

Treatment with morpholine at 125°–130° yields cis-1{N-[3-(4-morpholinyl-1,2,5-thiadiazol-3-yloxy)-2-hydroxypropylamino]cyclohexyl}-2-imidazolidinone.

The starting 3-chloro-4-(oxiranylmethyloxy)-1,2,5-thiadiazole is prepared as described in J. Med. Chem. 15, 651 (1972).

EXAMPLE 7

The following compounds of formula I wherein $R_1$ and $R_2$ combined represent ethylene, $R_3$ and $R_4$ represent hydrogen, and X represents oxygen, may be prepared according to procedures described in the previous examples.

| Example | Ar | R | Stereochemistry |
|---|---|---|---|
| 7/a | 1-naphthyl | H | cis |
| 7/b | 4-indolyl | H | cis |
| 7/c | 3-cyano-2-pyridyl | H | cis |
| 7/d | p-(carbamoylmethyl)phenyl | H | cis |
| 7/e | 3,4-dihydro-2(1H)—quinolon-5-yl | H | cis |
| 7/f | 5,6,7,8-tetrahydro-cis-6,7-dihydroxynaphth-1-yl | H | cis |
| 7/g | cis-o-(cyclopropylmethoxy)phenoxy | benzoyl | cis |
| 7/h | cis-o-(cyclopropylmethoxy)phenoxy | nicotinoyl | cis |
| 7/i | cis-o-(allyloxy)phenoxy | acetyl | cis |

The corresponding substituted optionally protected oxirane starting materials for compounds 7/a–7/f are reported in the available literature.

Compounds 7/g to 7/i may be prepared by acylation of compounds of Examples 1 and 3/m with benzoyl chloride, nicotinoyl chloride and acetyl chloride respectively, in pyridine solution.

EXAMPLE 8

A solution of 3.7 g of o-(allyloxy)phenoxymethyloxirane and 3.4 g of 1-(4-aminocyclohexyl)-3-ethylurea in 50 ml isopropyl alcohol is stirred at reflux for 3½ hours. The solution is concentrated in vacuo. The resulting crude product is purified by column chromatography using silica-gel and methylene chloride/methyl alcohol (first 200:15 then 1:1) as the eluent. The major slower moving component is dissolved in 30 ml isopropanol and 0.4 g of fumaric acid is added. The solution is concentrated to dryness and treated with 25 ml acetone, which is then decanted. The residue is dissolved in 25 ml of acetone and 2 ml methyl alcohol, and the solution is clarified by filtration. The product that crystallizes is filtered off, washed with a little acetone/methyl alcohol (9:1) and dried under high vacuum at 90° to give 1-{4-[3-(o-allyloxyphenoxy)-2-hydroxypropylamino]-cyclohexyl}-3-ethylurea hemifumarate, m.p. 159°–160°.

The starting material is prepared as follows:

To a solution of 6.3 g of 1-ethyl-3-(p-nitrophenyl)-urea in 75 ml of glacial acetic acid is added 3.2 g of 5% rhodium on alumina and the mixture is hydrogenated at 3 atmosphere pressure and 50° for 3½ hours. The catalyst is filtered off, the filtrate is evaporated to dryness. The residue is basified with 6N aqueous sodium hydroxide solution and extracted with methylene chloride (5×50 ml). The methylene chloride extract is evaporated to dryness, the residue is dissolved in 30 ml of isopropanol and a solution of hydrogen chloride in ethyl acetate is added to pH=1. On addition of 60 ml of ethyl ether, 1-(4-aminocyclohexyl)-3-ethylurea hydrochloride, m.p. 230°–232°, crystallizes.

A solution of 1.5 g of 1-(4-aminocyclohexyl)-3-ethylurea hydrochloride in 20 ml of methyl alcohol is treated with 0.36 g of sodium methoxide, to yield after usual workup 1-(4-aminocyclohexyl)-3-ethylurea as an oil which is used directly in the above condensation.

EXAMPLE 9

A solution of 2.67 g of 1-{4-[3-(o-cyclohexylphenoxy)-2hydroxypropylamino]-phenyl}-2-imidazolidinone in 50 ml acetic acid to which is added 1.75 g of 5% rhodium on alumina is hydrogenated at 3 atmospheres and 50° for 5 hours. After cooling to 20° the catalyst is filtered off and the filtrate concentrated to dryness. The residue is dissolved in 50 ml of water, the solution is basified with 6N aqueous sodium hydroxide while cooling in an ice bath and extracted with 75 ml of methylene chloride. The methylene chloride extract is washed twice with 25 ml of water, dried over anhydrous sodium sulfate, filtered and concentrated to dryness leaving a dark oil. The oil is dissolved in 30 ml of ethyl acetate and a solution of hydrogen chloride gas in ethyl acetate is added to pH=1. The supernatant is decanted from the gum that precipitates, the gum is dissolved in water, the aqueous solution is washed with ethyl acetate, the aqueous layer is basified with 10% aqueous sodium carbonate and extracted twice with 25 ml of ethyl acetate. The ethyl acetate extract is washed twice with water, dried over anhydrous sodium sulfate, filtered and concentrated in vacuo to yield a viscous oil. A 0.94 g portion of the oil is dissolved in 10 ml hot acetone and 0.13 g of fumaric acid is added; 2 ml of methyl alcohol is added to dissolve the precipitated gum, followed by 0.5 ml of water. The product that crystallizes is filtered off and dried in vacuo at 45° to yield cis 1-{4-[3-(o-cyclohexylphenoxy-2-hydroxypropylamino]cyclohexyl}-2-imidazolidinone hemifumarate hydrate, m.p. 117°–120°, identical to the compound of example 3/q.

The starting material is prepared as follows:

A mixture of 10 g of 1-(p-acetamidophenyl)-2-imidazolidinone (see Example 1), 10 g of sodium hydroxide and 100 ml of water is heated under reflux for four hours. The product that crystallizes on cooling is collected and recrystallized from ethanol to yield 1-(4-aminophenyl)-2-imidazolinone, m.p. 170°–2°.

A solution of 3.24 g o-(cyclohexyl)-phenoxymethyloxirane (see Example 3) and 2.65 g of 1-(4-aminophenyl)-2-imidazolidinone in 60 ml isopropanol is stirred at reflux for 18 hours. The reaction mixture is filtered and the filtrate concentrated in vacuo. The residue is dissolved in 50 ml ethyl acetate and acidified to pH=1 with a solution of hydrogen chloride gas in ethyl acetate. The supernatant is decanted from the dark gum that forms and the residue is treated with ethyl acetate and 5% aqueous sodium carbonate. The ethyl acetate solution is separated, washed with 10% aqueous sodium carbonate and twice with water. After drying over anhydrous sodium sulfate the solution is treated with charcoal, filtered and concentrated in vacuo leaving a dark viscous gum. The gum is chromatographed by passing through a column of silica gel using methylene chloride/methyl alcohol as eluent to yield 1-{4-[3-(o-cyclohexylphenoxy)-2-hydroxypropylamino]-phenyl}-2-imidazolidinone, which is used directly in the next step.

EXAMPLE 10

Preparation of 10,000 tablets each containing 10 mg of the active ingredient of Example 1:

| Formula: | |
|---|---|
| Cis-1-{4-[3-(o-allyloxyphenoxy)-2-hydroxy-propylamino]cyclohexyl}-2-imidazolidinone hemifumarate | 100.00 g |
| Lactose | 1,157.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 11

Preparation of 10,000 capsules each containing 10 mg of the active ingredient of Example 2:

| Formula: | |
|---|---|
| (S)—cis-1-{4-[3-o-(cyclopropylmethoxyphenoxy)-2-hydroxypropylamino]-cylohexyl}-2-imidazolidinone hemifumarate | 100.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine.

Analogously tablets or capsules are prepared from the remaining compounds of the invention, e.g., those illustrated by the examples herein.

EXAMPLE 12

A solution of 3.7 g of cis 1-(4-aminocyclohexyl)-2-imidazolidinone and 4.7 g of p-(cyclopropylmethoxy)-phenoxymethyloxirane in 50 ml of isopropanol is stirred at reflux for 6 hours. After standing at room temperature 16 hours, the solution is treated with 1.17 g of fumaric acid and heated at reflux for 30 minutes. A solid precipitates, the reaction mixture is cooled to room temperature, the product is filtered off, washed with isopropanol, and dried in vacuo at 65° to yield cis-1-{4-[3-(p-cyclopropylmethoxyphenoxy)-2-hydroxypropylamino]-cyclohexyl}-2-imidazolidone hemifumarate, m.p. 163°–165°.

The starting material is prepared as follows:

A mixture of 11.0 g of hydroquinone, 80 ml of isopropanol, 4.1 g of sodium hydroxide in 4.5 ml water, 9.9 g of cyclopropylmethyl chloride and 0.5 g of potassium iodide is stirred under reflux for 12 hours. The solvent is evaporated and the residue is extracted with ether. The ether extract is washed successively with water, sodium bicarbonate solution, dilute sodium bisulfite solution, water and sodium chloride solution and dried. The crude product obtained after evaporation of solvent is purified by preparative chromatography on silica gel, using first toluene and then toluene-ethyl acetate (90:5 to 85:15) as eluent to yield p-(cyclopropylmethoxy)-phenol, m.p. 49°–52°.

A mixture of 0.46 g of sodium hydroxide in 1.8 ml water and 14 ml ethanol, 1.64 g of p-(cyclopropylmethoxy)-phenol and 5.54 g of epichlorohydrin is stirred at room temperature in a nitrogen atmosphere for 24 hours and left at room temperature for 2½ days. The solvent is evaporated in vacuo and the residue is taken up in ether, washed with water and sodium chloride solution. After drying over anhydrous magnesium sulfate, the solution is filtered and concentrated under reduced pressure to yield p-(cyclopropylmethoxy)-phenoxymethyloxirane which is used directly in the condensation.

EXAMPLE 13

To a suspension of 3.8 g of lithium aluminum hydride in 100 ml tetrahydrofuran, 3.6 g of concentrated sulfuric acid is added dropwise at −5° to −10°. Stirring is continued for 1 hour at −5°, then 6.5 g of 3-(o-allyloxyphenoxy)-2-hydroxy-N-[4-(imidazolidin-2-on-1-yl)-cyclohexyl]-propionamide is added over a 5–10 minute period with stirring. The reaction mixture is allowed to warm to room temperature and stirred for an additional 18 hours, and finally refluxed for 1 hour. After cooling, the reaction mixture is quenched first with ethyl acetate, then with water and sodium hydroxide, filtered and concentrated in vacuo. The residue is dissolved in ethyl acetate. The solution is washed with water, dried and concentrated. The residue is dissolved in isopropanol and 0.9 g of fumaric acid added with stirring at reflux. After cooling cis-1-{4-[3-(o-allyloxyphenoxy)-2-hydroxypropylamino]-cyclohexyl}-2-imidazolidinone hemifumarate salt, the compound of Example 1, crystallizes.

The starting material is prepared as follows:

A mixture of 62 g of racemic chlorolactic acid, 82 g of o-allyloxyphenol and 90 g of 50% solution of sodium hydroxide in 500 ml of water is heated to 80°–90° with stirring for 2 hours. The hot mixture is acidified with concentrated hydrochloric acid and the crude product precipitates. After cooling it is filtered off and washed with water. The resulting 3-(o-allyloxyphenoxy)-2-hydroxypropionic acid can be recrystallized from a mixture of alcohol and water.

A solution of 40 g of phosgene in 100 ml of tetrahydrofuran cooled to 10° is added to a solution of 48 g of 3-(o-allyloxyphenoxy)-2-hydroxypropionic acid in 250 ml of tetrahydrofuran at room temperature with stirring. After standing for 18 to 24 hours at room temperature, the reaction mixture is concentrated in vacuo at a temperature below 40°. The residue is dissolved in acetone and cooled to −10°. A solution of 37 g of cis 1-(4-aminocyclohexyl)-2-imidazolidinone and 34 g of sodium bicarbonate in water is added slowly with stirring. After stirring for 2 hours at 20°, the reaction mixture is concentrated in vacuo to remove most of the acetone, then extracted repeatedly with methylene chloride. The methylene chloride solution is washed with water, dried and concentrated in vacuo to yield 3-(o-allyloxyphenoxy)-2-hydroxy-N-[4-(imidazolidin-2-on-1-yl)-cyclohexyl]-propionamide.

EXAMPLE 14

Sodium cyanoborohydride (0.6 g), 0.6 ml of glacial acetic acid and 3 g of molecular sieves are added to a solution of 2.5 g of 3-(o-allyloxyphenoxy)-2-hydroxypropylamine and 1.8 g of 1-(4-oxocyclohexyl)-2-imidazolidinone in 40 ml of anhydrous methanol. The reaction mixture is stirred for 72 hours. The pH is maintained at 4–5 throughout the reaction. The molecular sieves are filtered off, the filtrate is acidified with dilute aqueous hydrochloric acid to pH 2 and the methanol is removed in vacuo. The residue is extracted with ethyl acetate. The aqueous layer is basified with 6N NaOH, and extracted repeatedly with ethyl acetate. The ethyl acetate is removed in vacuo, the residue is dissolved in isopropanol and converted to the hemifumarate salt by addition of 0.6 g fumaric acid.

The resulting mixture of the cis and trans isomers of 1-{4-[3-(o-allyloxyphenoxy)-2-hydroxypropylamino]-cyclohexyl}-2-imidazolidinone hemifumarate is separated by recrystallization from isopropanol and/or ethanol to give the cis compound of Example 1.

The mixture of the cis and trans isomers of the free amine may first be separated by preparative chromatography and the cis free amine is then converted to the hemifumarate salt of Example 1.

The 3-(o-allyloxyphenoxy)-2-hydroxypropylamine starting material is prepared as follows:

A mixture of 50 g of o-(allyloxy)-phenoxymethyloxirane, 250 ml of concentrated ammonium hydroxide and 150 ml of isopropanol is stirred at room temperature for one week. The reaction mixture is filtered. Evaporation of the filtrate to a small volume, extraction with ethyl acetate and evaporation of the ethyl acetate extract yields a residue which is dissolved in hot isopropanol. Acidification with 4N ethanolic hydrogen chloride gives 3-(o-allyloxyphenoxy)-2-hydroxypropylamine hydrochloride, m.p. 106°–108°. The free base is obtained from this hydrochloride salt by basifying with ammonium hydroxide, extracting with methylene chloride and evaporating solvent to dryness; m.p. 81°–84°.

The 1-(4-oxocyclohexyl)-2-imidazolidinone starting material is prepared as follows:

A mixture of 18.3 g of 1-(4-aminocyclohexyl)-2-imidazolidinone as a mixture of cis and trans isomers, 2.0 g of benzyltributylammonium chloride, 250 ml of ethyl acetate and 360 ml of an aqueous 10% potassium hypochlorite solution [according to methodology as described by C. A. Meyers, J. Org. Chem. 26, 1046 (1961)] is stirred at room temperature for 1½ hours. The organic layer is separated and the aqueous layer is extracted with ethyl acetate. The pooled organic phases are washed with water, sodium bicarbonate solution and dilute hydrochloric acid, then dried and evaporated to dryness to yield 1-(4-oxocyclohexyl)-2-imidazolidinone.

EXAMPLE 15

Eye drops containing 0.1% of active ingredient:

| | |
|---|---|
| Cis-1-{4-[3-(o-allyloxyphenoxy)-2-hydroxy-propylamino]-cyclohexyl}-2-imidazolidinone | 1.0 g |
| hemifumarate | |
| 0.01 M citric acid | 370.0 ml |
| 0.02 M disodium phosphate | 620.0 ml |
| Disodium metabisulfite | 1.0 g |
| Benzalkonium chloride | 0.1 g |
| Hydroxypropylmethylcellulose | 5.0 g |
| Distilled water | quantity sufficient to 1000.0 ml. |

The ingredients are combined at room temperature. The resulting solution is filtered, sterilized and filled under sterile conditions into dropping bottles each containing 15 ml. of solution.

What is claimed is:

1. A compound of the formula

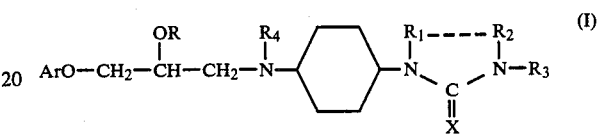

wherein the 1,4-cyclohexylene substituents are cis; Ar represents phenyl or phenyl substituted by one to three members selected from lower (alkyl, alkenyl, alkynyl, alkanoyl, mono-or di-alkylamino, alkanoylamino, alkylsulfonylamino, alkoxycarbonyl, alkylcarbamoyl, alkylisulfamoyl, alkoxy, alkylthio alkylulfinyl, alkylsulfonyl, alkenyloxy and alkynyloxy), hydroxy, cyano, halo, pyrrolyl, amino, 5 to 7-member (alkylene, oalkylene, thialkylene) imino, benzyloxy, phenyl, 5 to 7 membered cycloalkyl, carbamoyl, sulfamoyl, and from 3 to 7-membered cycloalyl-, phenyl-, hydroxy-, lower alkoxy-, lower alkoxycarbonylamino-, lower alkylthio-, lower alkylsufinyl-, lower alkylsulonyl- and carbamoyl-substituted (lower alkyl and lower alkoxy); R represents hydrogen, lower alkanoyl, nicotinoyl, benzoyl, or benzoyl substituted by one to three of lower alkyl, lower alkoxy, halo or trifluoromethyl; $R_1$ and $R_2$ represent hydrogen, or lower alkyl; or $R_1$ and $R_2$ combined represent unbranched or branched alkylene of 2 to 5 carbon atoms seperating the two nitrogen atoms thereto attached by 2 to 4 carbon atoms; $R_3$ and $R_4$ represent hydrogen or lower alkyl; and X represents O or S; or a pharmaceutically acceptable salt thereof.

2. A compound of formula

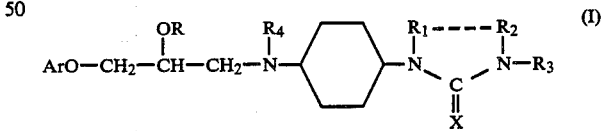

wherein the 1,4-cyclohexylene substituents are cis; Ar represents 1-naphthyl, 1(2H)-oxo-3,4-dihydronaphth-5-yl, 5,6,7,8-tetrahydro-cis-6,7-dihydroxynaphth-1-yl, 4-indolyl, 3,4-dihydro-2(1H)-quinolon-5-yl, 3-cyano-2-pyridyl, 4-(4-morpholinyl)-1,2,5-thiadiazol-3-yl; R represents hydrogen; $R_1$ and $R_2$ are combined to represent alkylene of 2 to 4 carbon atoms to form a 5-, 6-, or 7-membered ring; $R_3$ and $R_4$ represent hydrogen or lower alkyl; and X represents O or S; or a pharmaceutically acceptable salt thereof.

3. A compound according to claim 1, of the formula

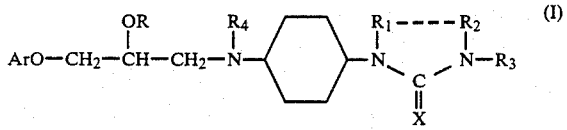

wherein the 1,4-cyclohexylene substituents are cis; Ar represents phenyl or phenyl substituted by one to three members selected from lower (alkyl, alkenyl, alkynyl, alkanoyl, mono- or ki-alkylamino, alkanoylamino, alkylsulfonylamino, alkoxycarbonyl, alkylcarbamoyl, alkylsulfamoyl, alkoxy, alkylthio, alkylsulfinyl, alkylsulfonyl, alkenyloxy and alkynyloxy), hydroxy, cyano, halo, pyrrolyl, amino, 5 to 7-membered (alkylene, oxalkylene, thialkylene)imino, benzyloxy, phenyl, 5 to 7-membered cycloalkyl, carbamoyl, sulfamoyl, and from 3 to 7-membered cycloalkyl-, phenyl-, hydroxy-, lower alkoxy-, lower alkoxycarbonylamino-, lower alkylthio-, lower alkylsulfinyl-, lower alkylsulfonyl- and carbamoyl-substituted (lower alkyl and lower alkoxy); R represents hydrogen; and $R_1$ and $R_2$ are combined to represent alkylene of 2 to 4 carbon atoms to form a 5-, 6-, or 7-membered ring; $R_3$ and $R_4$ represent hydrogen or lower alkyl; and x represents O or S; or a pharmaceutically acceptable salt thereof.

4. A compound of claim 1 of the formula

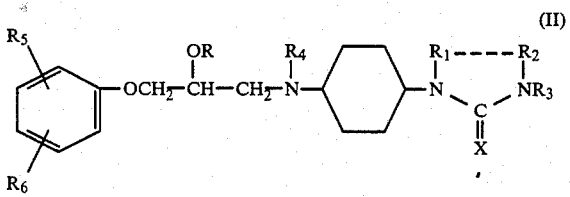

wherein the 1,4-cyclohexylene substituents are cis; R represents hydrogen or lower alkanoyl, $R_1$ and $R_2$ represent hydrogen; or $R_1$ and $R_2$ combined represent unbranched alkylene of 2 to 4 carbon atoms; $R_3$ and $R_4$ independently represent hydrogen or lower alkyl; each of $R_5$ and $R_6$ independently represents hydrogen, lower (alkyl, alkenyl, or alkynyl), lower (alkoxy, alkenyloxy or alkynyloxy), hydroxy, cyano, halo, amino, lower (mono- or di-alkylamino, alkanoylamino or alkylsulfonylamino), lower alkyl-(thio, sulfinyl or sulfonyl), morpholino, 1- or 2-pyrrolyl, phenyl, 5 to 7-membered cycloalkyl, lower alkanoyl, lower alkoxycarbonyl, carbamoyl, or sulfamoyl; $R_6$ also represents lower (alkyl or alkoxy) substituted by a member selected from cycloalkyl of 3 to 6 carbon atoms, from phenyl, from lower alkoxy, from hydroxy, from lower alkoxycarbonylamino, from lower alkyl-(thio, sulfinyl and sulfonyl), and from carbamoyl; X represents O or S; or a pharmaceutically acceptable salt thereof.

5. A compound of claim 4 of the formula

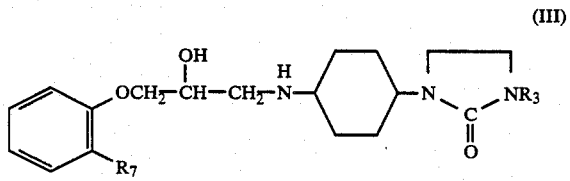

wherein the 1,4-cyclohexylene substituents are cis; $R_3$ represents hydrogen or lower alkyl; $R_7$ represents cyano, lower alkoxycarbonyl, pyrrolyl, morpholino, alkenyloxy of 3 to 6 carbon atoms, alkynyloxy of 3 to 6 carbon atoms, or alkoxy of 1 to 3 carbon atoms substituted by cyclopropyl; or a pharmaceutically acceptable salt thereof.

6. A compound of claim 5 wherein the carbon bearing the hydroxy group is in the S-configuration.

7. A compound of claim 5 wherein $R_3$ represents hydrogen; $R_7$ represents allyloxy, propargyloxy or cyclopropylmethoxy; a stereoisomer or enantiomer thereof; or a pharmaceutically acceptable acid addition salt thereof.

8. A compound of claim 5 being cis-1-{4-[3-(o-allyloxyphenoxy)-2-hydroxypropylamino]-cyclohexyl}-2-imidazolidinone or a pharmaceutically acceptable acid addition salt thereof.

9. A compound of claim 5 being cis-1-{4-[3-(o-cyclopropylmethoxyphenoxy)-2-hydroxypropylamino]-cyclohexyl}-2imidazolidinone; the S-enantiomer; or a pharmaceutically acceptable acid addition salt thereof.

10. A compound of claim 5 being cis-1-{4-[3-(o-pyrrolylphenoxy)-2-hydroxypropylamino]-cyclohexyl}-2-imidazolidinone or a pharmaceutically acceptable acid addition salt thereof.

11. A pharmaceutical composition useful for the treatment of hypertension or cardiac disorders comprising an effective amount of a compound of claim 1 in combination with one or more pharmaceutically acceptable carriers.

12. A pharmaceutical composition useful in the treatment or prevention of diseases responsive to adrenergic blockade in mammals comprising an effective adrenergic blocking amount of a compound of claim 1, in combination with one or more pharmaceutically acceptable carriers.

13. A method of treating diseases responsive to adrenergic receptor blockade in mammals comprising the administration to a mammal in need thereof of an effective amount of an adrenergic blocking compound of claim 1, in combination with one or more pharmaceutically acceptable carriers.

14. A method of treating hypertension or cardiac disorders in mammals comprising the administration to a mammal in need thereof of an effective amount of a compound of claim 1, in combination with one or more pharmaceutically acceptable carriers.

15. A method of treating glaucoma comprising the topical administration to a mammal in need thereof of an effective intraocular pressure-lowering amount ot a compound of the formula

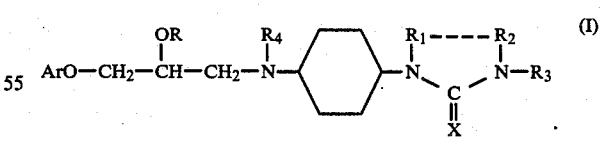

wherein Ar represents phenyl or phenyl substituted by one to three members selected from lower alkyl, alkenyl, alkynyl, alkanoyl, mono- or di-alkylamino, alkanoylamino, alkylsulfonylamino, alkoxycarbonyl, alkylcarbamoyl, alkylsulfamoyl, alkoxy, alkylthio, alkylsulfonyl, alkenyloxy and alkynyloxy, hydroxy, cyano, halo, pyrrolyl, amino, 5 to 7-membered (alkylene, oxalkylene, thialkylene)imino, benzyloxy, phenyl, 5 to 7-membered cycloalkyl, carbamoyl, sulfamoyl, and from 3 to 7-membered cycloalkyl-, phenyl-, hydroxy-, lower alkoxy-, lower alkoxycarbonylamino-, lower alkylthio-, lower alkylsulfinyl-, lower alkylsulfonyl- and carbamoyl-substituted (lower alkyl and lower alkoxy); R represents hydrogen, lower alkanoyl, nicotinoyl, benzoyl, or benzoyl substituted by one to three of lower alkyl, lower alkoxy, halo or trifluoromethyl; $R_1$ and $R_2$ represent hydrogen or lower alkyl; or $R_1$ and $R_2$ combined represent unbranched or branched alkylene of 2 to 5 carbon atoms separating the two nitrogen atoms thereto attached by 2 to 4 carbon atoms; $R_3$ and $R_4$ represent hydrogen or lower alkyl; and X represents O or S; or a pharmaceutically acceptable salt thereof; in combination with one or more pharmaceutically acceptable carriers.

16. A method according to claim 15 of treating glaucoma comprising the topical administration to a mammal in need thereof of an effective intraocular pressure-lowering amount of a compound of the formula

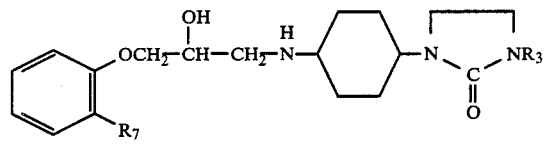

(III)

wherein $R_3$ represents hydrogen or lower alkyl; $R_7$ represents cyano, lower alkoxycarbonyl, pyrrolyl, morpholino, alkenyloxy of 3 to 6 carbon atoms, alkynyloxy of 3 to 6 carbon atoms, or alkoxy of 1 to 3 carbon atoms substituted by cyclopropyl; or a pharmaceutically acceptable salt thereof, in combination with one or more pharmaceutically acceptable carriers.

17. A method according to claim 16 of treating glaucoma comprising the topical administration to a mammal in need thereof of an effective intraocular pressure-lowering amount of a compound of the formula III wherein $R_3$ represents hydrogen; $R_7$ represents allyloxy, propargyloxy or cyclopropylmethoxy; a stereoisomer or enantiomer thereof; or a pharmaceutically acceptable acid addition salt thereof; in combination with one or more pharmaceutically acceptable carriers.

18. A method according to claim 17 wherein the compound is cis-1-{4-[3-(o-allyloxy-phenoxy)-2-hydroxypropylamino]-cyclohexyl}-2-imidazolidinone or a pharmaceutically acceptable acid addition salt thereof.

19. A method of treating glaucoma comprising the topical administration to a mammal in need thereof of an effective intraocular pressure-lowering amount of a compound of the formula

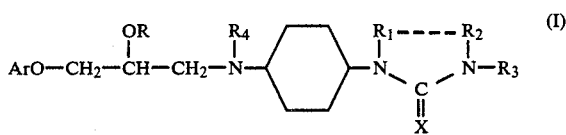

(I)

wherein Ar represents 1-naphthyl, 1(2H)-oxo-3,4-dihydronaphth-5yl, 5,6,7,8-tetrahydro-cis-6,7-dihydroxynaphth-1-yl, 4-indolyl, 3,4-dihydro-2(1H)-quinolon-5-yl, 3-cyano-2-pyridyl, 4-(4-morpholinyl)-1,2,5-thiadiazol-3-yl; R represents hydrogen; $R_1$ and $R_2$ are combined to represent alkylene of 2 to 4 carbon atoms to form a 5-, 6-, or 7-membered ring ; $R_3$ and $R_4$ represent hydrogen or lower alkyl; and X represents O or S; or a pharmaceutically acceptable salt thereof; in combination with one or more pharmaceutically acceptable carriers.

20. A method of treating glaucoma comprising the topical administration to a mammal in need thereof of an effective intraocular pressure-lowering amount of a compound of claim 7 in combination with one or more pharmaceutically acceptable carriers.

* * * * *